United States Patent [19]
Wilson et al.

[11] Patent Number: 5,236,135
[45] Date of Patent: Aug. 17, 1993

[54] MEDICAL WASTE TREATMENT SYSTEM

[75] Inventors: Joseph H. Wilson, Speedway; David B. Mennel; Jeffrey C. Rapp, both of Greenwood, all of Ind.

[73] Assignee: ECOMED, Inc., Indianapolis, Ind.

[21] Appl. No.: 882,915

[22] Filed: May 19, 1992

Related U.S. Application Data

[63] Continuation-in-part of Ser. No. 704,455, May 23, 1991.

[51] Int. Cl.⁵ .............................................. B02C 19/12
[52] U.S. Cl. ........................................ 241/21; 241/99; 241/199.12; 241/282.2; 241/285.1; 241/606; 99/510; 366/314; 220/373
[58] Field of Search ................. 241/99, 199.12, 282.1, 241/282.2, 21, 92, 285.1, 606; 99/510; 366/314; 220/373; 215/261, 308

[56] References Cited

U.S. PATENT DOCUMENTS

| | | | |
|---|---|---|---|
| 1,592,601 | 7/1926 | Hines | 241/282.2 |
| 2,635,784 | 4/1953 | Bering et al. | 220/373 |
| 2,820,595 | 1/1958 | Schumacher | 241/100 X |
| 3,156,278 | 11/1964 | Otto | 241/282.2 |
| 3,901,349 | 8/1975 | DeNoyer | 241/100 X |
| 4,269,364 | 5/1981 | Moriconi et al. | 241/99 X |
| 4,586,666 | 5/1986 | Fox | 241/199.12 X |
| 4,637,561 | 1/1987 | Edberg | 241/154 |
| 4,816,307 | 3/1989 | Honeycutt | |
| 4,852,814 | 8/1989 | Amiot et al. | 241/282.2 X |
| 4,878,627 | 11/1989 | Otto | 241/199.12 |
| 4,984,748 | 1/1991 | Kimura | 241/100 |
| 5,054,696 | 10/1991 | Mennel et al. | 241/99 X |

FOREIGN PATENT DOCUMENTS

| | | | |
|---|---|---|---|
| 1394972 | 3/1965 | France | 241/282.1 |
| 1025432 | 2/1986 | Japan | 241/282.1 |
| 725700 | 4/1980 | U.S.S.R. | 241/282.1 |
| 1142167 | 2/1985 | U.S.S.R. | 241/282.1 |
| 1546076 | 2/1990 | U.S.S.R. | 241/282.1 |

*Primary Examiner*—Mark Rosenbaum
*Assistant Examiner*—Frances Chin
*Attorney, Agent, or Firm*—Willian Brinks Olds Hofer Gilson & Lione

[57] ABSTRACT

A method and apparatus for the treatment of contaminated medical waste, including solid and non-solid, potentially infectious materials, permits the collection of such medical waste at the point and at the time of its generation in a solid container, which is subsequently transported for pulverization, disinfection and safe disposal. A separate portable processing chamber, with an integral means to treat medical waste, is used at locations remote from its power unit for the collection of medical waste and then moved to the location of the power unit to drive the waste-treatment means within the chamber. The separate waste collection and treatment assembly includes a closable chamber, a rotating waste treatment system that is rotatably carried within the chamber by bearings spaced on a supporting cylinder carried by the chamber bottom, a plurality of pivotable blades that are carried by a rotating system and have a configuration which, in cooperation with surfaces of the chamber walls, provide effective disintegration, pulverization and blunting of solid waste and cutting and mincing of non-solid waste, and the circulation and disinfection of the medical waste within the separate chamber.

36 Claims, 10 Drawing Sheets

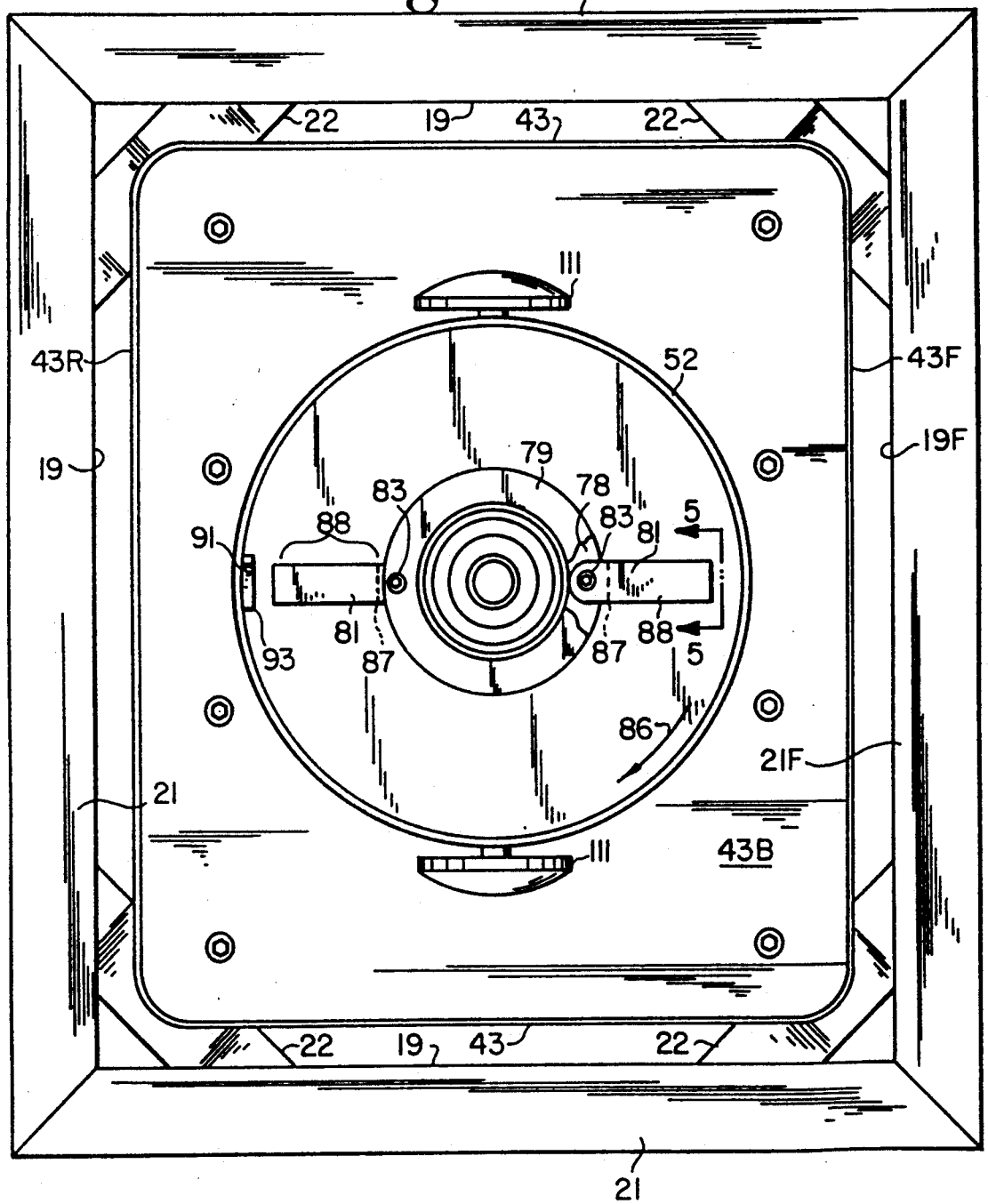

MEDICAL WASTE TREATMENT SYSTEM

This is a continuation-in-part of U.S. patent application Ser. No. 07/704,455 filed May 23, 1991 entitled Medical Waste Treatment Device and Method.

FIELD OF THE INVENTION

This invention relates generally to methods and apparatus for disintegrating trash materials, and more particularly to methods and apparatus for decontaminating and rendering infectious solid and soft medical waste items handleable.

DESCRIPTION OF THE PRIOR ART

A great variety of equipment has been devised for disposing of trash of various kinds and sizes. Examples could range from a hammer as a simple example, to an automobile shredder as a more complex example. Of greater interest to the treatment of medical waste is the machine disclosed in U.S. Pat No. 4,619,409 issued Oct. 28, 1986. It is a comparatively large stationary machine for disintegration and decontamination of hospital waste materials in relatively large volumes. But there are many facilities which do not have such volumes of waste materials, space for such a large machine, or funds to buy such large and expensive machines. A couple of examples are medical and dental offices. One effort to deal with the waste materials of such facilities is represented in U.S. Pat. No. 4,971,261 issued Nov. 20, 1990 to Solomons. That patent discloses a device that is intended to be a portable desk-top device. It has a cylindrical body 11, cover 12, one-way feed opening 13 in the cover 12, a motor driven rotating blade 20 in the body to fragment the 12 which can be rotated to a position of registry with a discharge opening 14 in the cylindrical body 11 and which communicates with the disposal chute 15 for discharge of the fragmented particles into the jar 23 which contains sterilizing solution. Then the jar, with sanitized and fragmented items is said to be disposed of as ordinary trash Solomons apparently was not intended to deal with soft waste items Also, the decontamination treatment is not done until after the fragmenting.

The waste from a physician's or dentist's office and for which safe disposal is needed, includes not just hard items such as needles, syringes and vials, but also soft items such as bandage material and rubber gloves. It is desirable to avoid the necessity of sorting these things before disposal. The existing prior art equipment in a size suitable for portable, desk-top or counter-top use in a comparatively small facility, cannot suitably handle such a variety of materials.

SUMMARY OF THE INVENTION

The invention provides a method and apparatus for the treatment of contaminated medical waste, including such solid items as syringes and needles, glassware, tubes, vials, culture plates and specimens, and disposable scalpels, and such soft and fibrous materials as gloves and masks. This invention permits the collection of such medical waste at the point and at the time of its generation in a container, which cannot be pierced or torn by the solid waste and in which the waste is subsequently transported, pulverized and disinfected for easy disposal.

The invention eliminates repeated handling of the medical waste and the associated danger of the inadvertent transmission of infectious diseases resulting from the handling of such waste. The invention permits these substantial safeguards to be enjoyed by those personnel working in smaller doctor's and dentist's offices and smaller clinics, which often do not have access to proper medical waste processing facilities, without unnecessary expense and duplication of apparatus.

The apparatus of the invention provides a separate portable processing chamber, with an integral means to treat medical waste, that can be used at locations remote from its power unit for the collection of medical waste and then moved to the remote location of the power unit to drive the waste-treatment means within the chamber for pulverizing and disinfecting the medical waste within the chamber without danger to medical or operating personnel.

The apparatus of the invention comprises a separate waste collection and processing assembly including a closable chamber for the collection, pulverization and disinfection of medical waste. A rotating waste treatment system is rotatably carried within the chamber by bearings spaced on a supporting cylinder that is carried by the chamber bottom around a centrally located aperture through which the rotating system is driven. The rotating waste treatment system includes a plurality of pivotable blades that are carried by a rotating hub and have a configuration which, in cooperation with the chamber walls, provides effective disintegration, pulverization and blunting of solid waste and cutting and mincing of non-solid waste, and the circulation and disinfection of the medical waste within the separate chamber. An inner surface configuration of the chamber provides surfaces coating with the rotating blades to destroy the waste material and effectively directs the waste during its destruction and disinfection. Furthermore, the separate chamber is self-cleaning and provides collection means from which the destroyed and disinfected waste material may be easily poured In preferred systems of the invention, an imperforable but breakable container is adapted to receive and contain used and possibly infectious solid waste, such as hypodermic needles, at a site of their use and thereafter permits their safe handling in the container, and the apparatus is adapted to permit the insertion of the imperforable but breakable container into its chamber carrying the used hypodermic needles, and for the destruction and disinfection of the breakable container and the used hypodermic needles that it safely contained while outside of the chamber.

Preferred apparatus of the invention further include rigid fenders carried by the rotating waste treatment system in front of the pivotable blades and extending downwardly to a small clearance from the chamber bottom, to sweep soft waste from adjacent the rotating hub and prevent it from collecting and being carried under the rotating hub. The fenders can be raked in the direction of rotation and provide blade impingement surfaces to prevent the blades from pivoting forwardly in the direction of rotation past a radial line extending outwardly from their pivotal mountings. In addition, the fender-forming surfaces can extend upwardly on the rotating hub within the chamber to provide one or more rotating surfaces to fractionalize the breakable containers that carry used hypodermic needles and other solid waste.

In addition, a radially extending surface can be provided in the waste treatment chamber sidewall which is positioned to direct waste material at the abutment bar for destruction by the coaction of the abutment bar surfaces and the pivotable blades of the rotating waste treatment assembly.

In preferred apparatus of the invention, the waste destruction and disinfection chamber is closed by a removable filter cap carrying a high efficiency particulate air filter that permits the escape of air and water vapor from the chamber during the operation while trapping aerosols and fine particles.

Preferred apparatus of the invention also comprise means for reducing the vibration and sound that results from operation of the rotating waste destruction system by inhibiting its transfer to and escape from the apparatus enclosure. In preferred apparatus, the motor that drives the rotating waste treatment assembly within the waste treatment chamber is surrounded by a walled enclosure and by an enclosure bottom with a central opening for motor cooling air. An elastomeric cylinder is provided between the motor and the enclosure bottom, surrounding the cooling air opening and having sufficient length to be slightly compressed between the motor and the enclosure bottom and to form a cooling air duct leading to the motor and a sound muffler. Preferred apparatus can also include means for isolating the waste treatment chamber and its driving motor from their supporting enclosure. Such means can include a support plate to carry both the waste treatment chamber and the driving motor for the waste treatment assembly, a pair of isolating straps to carry the support plate from the enclosure and a plurality of vibration absorbing mounts for carrying the support plate on the isolating straps.

Other features and advantages of the disclosed embodiments and methods of the invention will be apparent from the drawings and more detailed description of the invention that follows.

BRIEF DESCRIPTION OF THE DRAWINGS

FIG. 4 is a section taken at line 4—4 in FIG. 2 and viewed in the direction of the arrows;

FIG. 5 is an end view of a blade taken at line 5—5 in FIG. 4 and viewed in the direction of the arrows;

FIG. 6 is a perspective view of a strainer plug used in the practice of the invention;

DESCRIPTION OF THE PREFERRED EMBODIMENT

Figure 1:
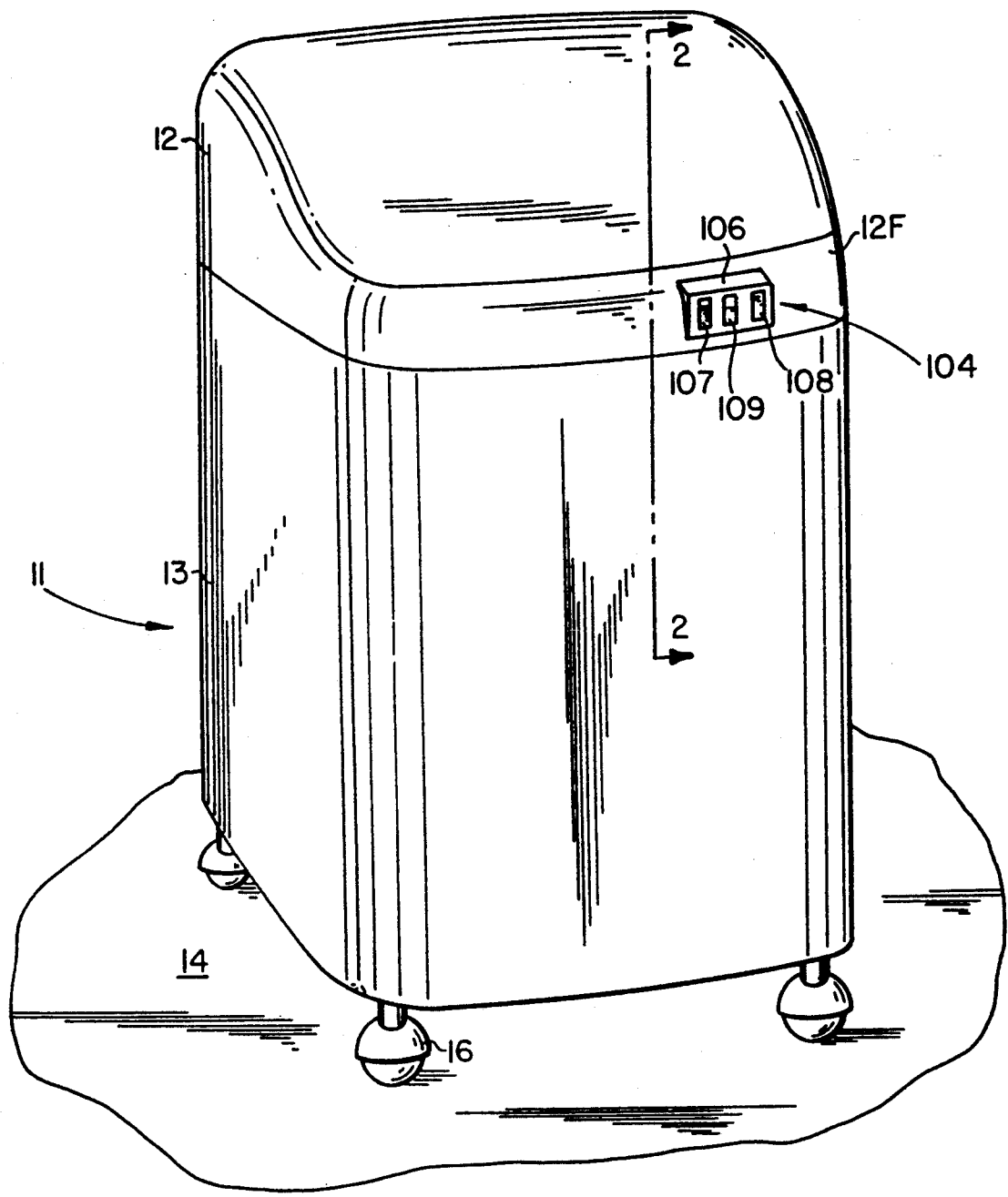
FIG. 1 is a pictorial view of a portable waste treatment device according to the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, and particularly FIG. 1, a floor-mounted, mobile unit 11 includes a main cabinet 12 mounted on the top of a cart 13 which is movable along the floor 14, being supported on four casters 16, one at each corner. Referring now to FIG. 3, and regardless of whether a mobile cart 13 or a stationary counter top is the site for the present invention, it will include a support 17 which, in the illustrated embodiment, is rectangular in shape, framing a central opening 18 in which the waste treatment device is mounted according to the present invention. For this purpose, a rectangular frame 19, typically metal, is provided with an outwardly extending perimetrical flange 21 (FIGS. 2 and 4) and is mounted on the support 17 and may be secured to it in any suitable manner. The portions of frame 19 and flange 21 that are at the front of the machine are designated 19F and 21F. Frame 19 has a gusset 22 welded to it at each of the four corners of the frame. An isolation strap 23 having a front end 23F and rear end 23R is mounted to the frame gussets 22 at their respective ends by means of isolator couplings 24. An identical strap 25 and mounting arrangement is provided at the opposite side of the frame 19.

A motor mount plate 26 is mounted on top of the two straps, with four fasteners 27 securing each side of the plate to each of the two straps 23 and 25. In the illustrated example, the fasteners are socket head cap screws with nuts. This motor mount plate is generally U-shaped as shown best in FIG. 2. The motor 28, having a standard C-face 29, is fastened to the bottom center of the plate 26 by four socket head cap screws 31. The motor shaft 32 extends up through a central aperture 33 in plate 26 and is provided with a slinger ring 34 immediately above the plate 26. The motor shaft has a standard square keyway to receive a standard square key 37 in coupling 38 to which the key is secured by set screw 39. The upper end of the coupling 38 is provided with a ½ inch square cross section at 41.

The outwardly turned front and rear flanges 26F and 26R, respectively, of the motor mount plate support the main cabinet 12. The cabinet has a front wall 12F, and a rear wall 12R and is molded in one piece of fiberglass reinforced plastic with a generally centralized tub portion 42 which is generally rectangular in configuration as shown by the front and rear walls 43F and 43R, respectively, and the sidewalls 43 in FIG. 4. The floor 43B of the tub is secured to the outwardly extending flanges 26F and 26R of the motor mounting plate by four fasteners 44 through each of the flanges, these fasteners typically being socket head cap screw and nut assemblies.

A hollow bulb gasket 46 is secured to the inside of the cabinet outer shell around the entire perimeter of the lower edge 47 of the shell. This gasket 46 lightly but sealingly engages the top surface of the support 17 entirely around the perimeter of the cabinet. However, it does not provide support for the cabinet since that is supported by the motor mount plate supporting the bottom 43B of the cabinet tub portion.

The flask assembly 51 of the present invention includes a flask lower housing 52 and flask top housing 53, both of which are symmetrical about the central axis 54. The flask lower housing has an outwardly turned upper circular flange 52U supporting an O-ring 56 which supports the circular bead at the bottom of the flask top housing. The top and lower housings are fastened together by over-center lever operated spring clamps 57 such as are available from Dzus Fasteners of West Islip, N.Y. 11795. The bottom of the flask lower housing has four circularly spaced feet 58 which are received in sockets 59 in the floor 43B of the cabinet tub portion. These feet support the flask assembly in the cabinet tub. They also prevent the flask assembly from rotating in the tub.

An impeller assembly 61 is mounted in the flask assembly. It is located and supported by a bearing mount cylinder 62 which is welded to the bottom of the flask lower housing at 63 around the central opening 64 in the flask bottom. This bearing mount cylinder receives the lower ball bearing assembly 66 and the upper ball bearing assembly 67. The inner race of each of these ball bearing assemblies fittingly receives outer cylindrical surfaces of the impeller shaft 68 which has an octagonal internal spline or socket at 69 received on the square upper end of the coupler 38. The upper portion of the impeller shaft has a sleeve 71 pressed thereon above the inner race of the upper bearing 67. This serves to engage a lip seal 72 which is secured in the outer race receiving bore of the impeller bearing mount cylinder 62. The upper end of shaft 68 is threaded at 73 and threadedly receives thereon the top 74 of the impeller which extends from the top down to the slinger flange 76 at the bottom and which is immediately above the bottom of the flask lower housing. The cylindrical wall 77 of the impeller has two additional circular flanges above the slinger flange 76. These are the blade support flange 78 and the blade hub cover flange 79. Two blades 81 are mounted in the annular groove 82 between the flanges 78 and 79 and pivotally secured in place by the pins 83 which are shoulder bolts screwed into the flange 78. The shape of these blades can be observed in FIG. 4 and FIG. 5. The blades are driven in the clockwise direction of arrow 86 in FIG. 4. Although the hub area of the blade is rectangular as shown in FIG. 5, the blade is tapered beginning at a line 87 (FIG. 4) to provide a sharp leading edge 88 while the trailing edge of the blade 89 is the full height of the hub portion. The blade is made of a tungsten carbide compound.

A "baffle" bar 91 is mounted on the inside upstanding cylindrical wall of the flask lower housing and extends up from near the bottom to a top edge 92. Thus, it presents a 90° angle edge 93 facing the materials as they are driven around by the impeller blades moving in the clockwise direction of arrow 86. Due to the inclination of the lower face of the blades 81 downward from the front or leading edge toward the rear or trailing edge, as the blades 81 rotate the trailing edge of each is closer to the bottom of the flask than is the sharp leading edge. This drives the waste materials downward and thus assures that they will be aggressively treated by the baffle bar 91 during operation.

A removable flask cap 96 is provided in the central opening 97 at the top of the frustoconical surface of the flasktop housing. This cap 96 has a tapered wall 98 so as to be manually insertable to the point of a snug fit, but can be readily removed manually, if desired, by means of the outwardly directed circular flange 99 at the top of the cap. The cabinet is provided with a lid 101 which is hinged to the upper rear wall 12R of the cabinet by adjustable hinges 102 such as the 500 Series marketed by Southco, Inc. of Concordville, Pa. 19331. These hinges are adjustable so that the lid can be raised at the front end edge in the direction of arrow 102a can remain in virtually any position up to vertical. The underside of the lid has an inwardly projecting bulge 103 therein which, when the lid is closed, engages the flask cap 96 and assures that the cap will remain securely closed in place on the flask top housing. A bulb gasket may be provided around the perimeter of the cabinet lid to seal against the cabinet top during operation.

Referring to FIG. 6, a strainer cap 112 is shown. It is similar to cap 96, having a tapered wall 113 and perimetrical top flange 114 but, instead of a solid bottom, the bottom 116 is a screen. It may also have a handle tab 117 at the top flange.

Referring again to FIGS. 1 and 2, a control group 104 is provided on a boss 106 at the front of the cabinet and includes a momentary contact "ON" switch 107, and "EMERGENCY STOP" switch 108, and a pilot light 109 illuminated when the operating cycle is in progress. These are associated with suitable electrical circuitry to control the motor as desired. The circuitry is not shown herein as it may be conventional and well within the skill of the art.

Referring again to FIG. 4, a pair of T-type handles 111 may be provided on the side of the flask lower housing for a purpose which will be described now.

OPERATION

The flask assembly is removable from the main cabinet by simply lifting the cabinet lid and lifting the flask assembly out of the cabinet by use of the T-handles, one in each hand. The flask assembly can be easily lifted off the coupler and moved to whatever site location is convenient for deposit of medical waste material into it, wherever such material is being generated. Of course, if the unit is mounted on a moveable cart as in FIG. 1, the cart can be simply pushed to the site without removing the flask assembly from it. With the top cap 96 pulled out of the top of the flask assembly, the waste material can be simply dropped into the flask assembly through the to opening 97. The opening is large enough in diameter, four inches, for example, to readily receive syringes, bandage material, rubber gloves, culture plates and vials, for example Such waste materials can be dropped directly into the opening as they are produced, rather than putting them in another container and then transferring them later to the flask. For example, as a bandage is removed from a subject, the bandage materials are placed directly into the flask. When the flask assembly has been filled to a level about even with the top of the flask lower housing or bowl 52, and if the flask assembly is separate from the main cabinet, it can then be returned to the main cabinet and placed on the cabinet tub bottom with the four feet 58 in the pockets 59.

Simultaneously the impeller shaft socket is received on the coupler square 41. Then water is poured through the top opening 97, a pouch of decontaminant is added, and the top cap 96 is installed and the cabinet lid is closed. Then the start switch 107 is pushed. The lid may thereupon be locked by an automatic electrically operated lid latch (not shown). The motor is energized and drives the impeller. The blades are driven thereby in a circular path, clockwise as per arrow 86 in FIG. 4 around the impeller axis. As they do so, they begin to cut-up the waste material in the housing. Although the materials do provide some resistance to the blade action, the combined effects of the sharp leading edges 88 of the blades, and the centrifugal force, keep them deployed in a radially outward extending direction to continue to cut up the waste material. As this occurs, the slinger flange 76 at the bottom of the impeller assembly keeps the material moving outward and upward around the curved outer portion 55 of the flask lower housing wall 52. Thus, it is kept moving in a path outward and upward along the wall and then back down into the blades. Also, the presence of the vertical block (baffle) 91 provides an abutment which, to materials moving in the clockwise direction, is relatively sharp. In addition, it inhibits the free circular flow of material around the inner wall of the flask lower housing, tending to direct it back into the path of the blades. The baffle 91 facilitates destruction of sharp items and facilitates cutting of soft materials. This processing continues as long as desired until it is either stopped by expiration of the "run" period of an automatic timer, or is manually stopped by pushing the emergency stop pad 108 to simply nd the desired cycle. The pilot light serves as an indicator that a cycle is in process. This light may remain on for several minutes after the processing is complete in order to indicate to the operator that it is not yet time to open the lid, because the contents have not yet settled.

When the pilot light goes out, the operator can then open the lid, grip the T-handles, pull the flask assembly out of the tub of the main cabinet, and take it to a sink. The cap 96 is removed and replaced by the strainer 112 in the opening 97. Then the flask assembly is inverted in the sink, and the decontaminant solution, together with any other liquids which were contained in the waste material are drained into the sink. Then the flask assembly is righted and moved over to a solid waste receiver bucket or bag or the like, and the processed waste materials are dumped into the receiver for later disposal in a conventional waste container.

As a preferred alternative procedure, instead of using the strainer, the flask assembly can be dumped, liquids and solids simultaneously, into a disposable bag containing a liquid-absorbent gel compound. Then the flask is righted and ready for return to the waste generation site for collection of more waste in it.

With a machine built according to the present invention, in addition to the mincing action on materials, needles are bent and blunted as they are driven into the baffle 91. If it is ever desired to do so, the flask can be washed out without taking it apart, just as one could wash out a vase or bowl. If ever desired, such as for servicing interior components, the flask upper and lower housing can be separated by releasing the spring clamps 57. After servicing, they can be re-assembled, clamped together, and the flask assembly can be returned to the waste generation site for use again as described above.

As an example, the chamber forming flask components can be made of spun stainless steel. Many of the more dense components, such as the impeller bearing mount cylinder, the impeller shaft, and the impeller itself, can be stainless steel investment castings. For a flask assembly that will hold and process approximately one-two gallons of medical waste materials in their final processed state, a drive motor of two horsepower is useful to complete a processing of that much material within a two to three minute cycle. A rotational speed of about 3450 r.p.m. is advisable for effective destruction of the solid and soft medical waste identified above. Examples of suitable decontaminant solutions are a one ounce package of A-33 dry decontaminant powder as marketed by Airkem Professional Products of St. Paul, Minn. and an Iodophor disinfectant compound sold by Ecomed, Inc. at Indianapolis, Ind. under their trade name Mikroklene. Dumping of treated waste from the flask can be into a plastic bag of appropriate size and at least three mil membrane, and preferably an eight gallon, double ply plastic bag, which contains a polymeric absorbent powder which develops a gel as it absorbs the liquid. The bag preferably has a drawstring for convenient handling and can be placed in a conventional trash or garbage container. Although the description refers to a one-gallon flask or chamber, it should be appreciated that the present invention can be applied to larger or smaller size apparatus.

Figure 7:
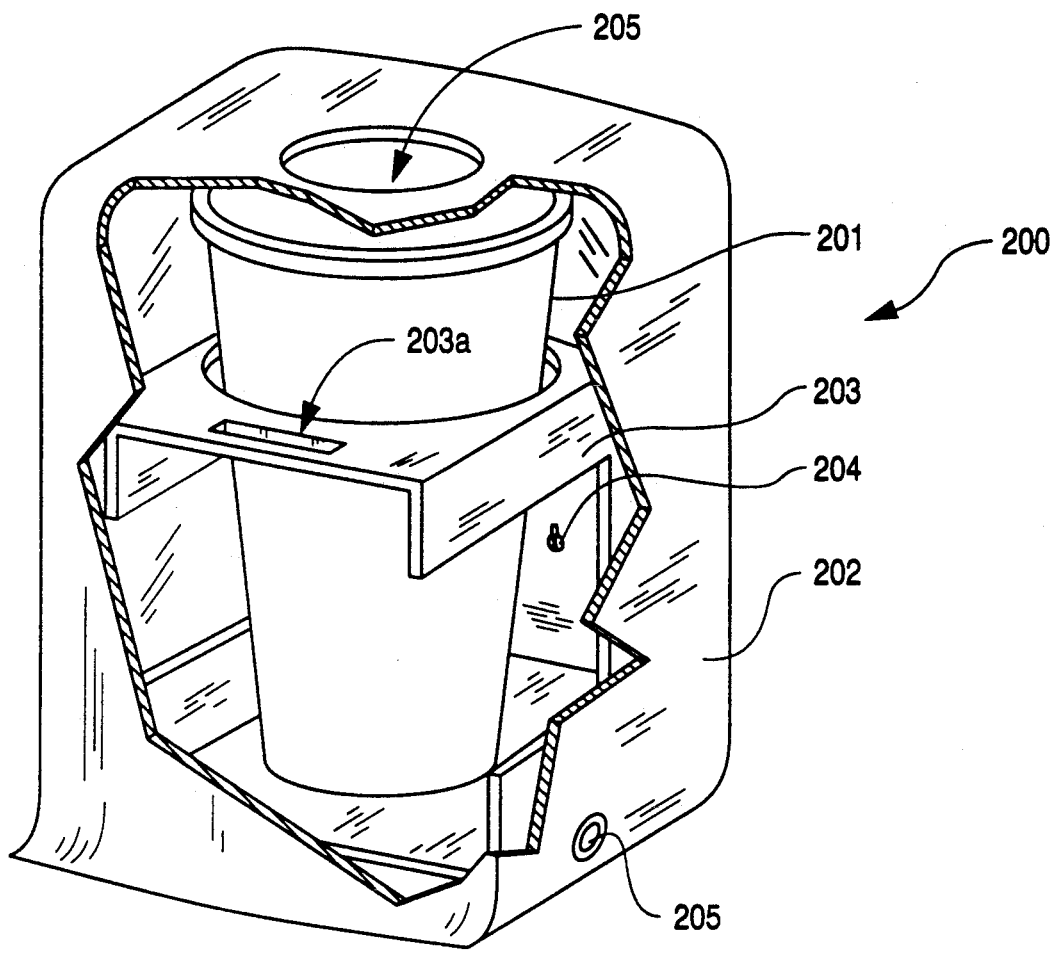
FIG. 7 is a partially broken away perspective view of a collection station for medical waste such as used and possibly infectious hypodermic needles.
Figure 7A:
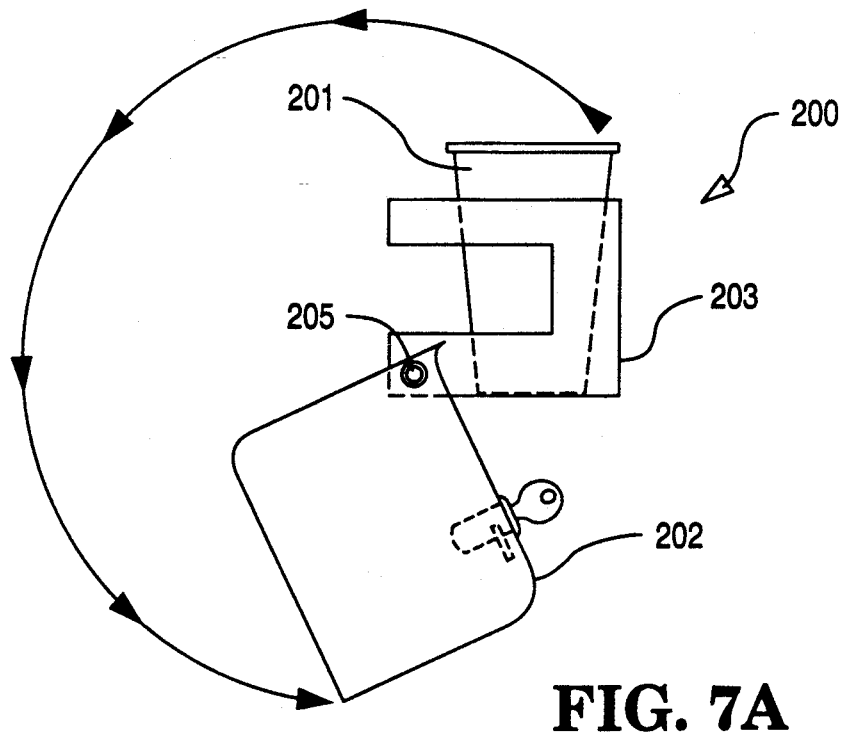
FIG. 7A is a diagrammatic drawing of an open collection station.

Preferred systems of the invention can include the use of an imperforable but breakable container, which is particularly adapted to receive and contain used and possibly infectious, sharp solid waste, such as used hypodermic needles. Such a container, or containers, may be located at the locations in which blood samples are taken or injections are given for the collection of the possibly infectious used hypodermic needles. FIG. 7 is a partially broken away perspective drawing showing a collection station 200 for used hypodermic needles that includes such an imperforable but breakable container 201. As shown in FIG. 7, the collection station can comprise a lockable housing 202 including an inner mounting bracket or plate 203 adapted to be fastened to the wall for example, by a plurality of screws 204. The hinged cover 202 includes an orifice 205 permitting medical personnel to insert used hypodermic needles and other medical waste into the container 201. The lockable housing 202 comprises a hinged lockable cover (partially broken away in FIG. 7) which may be pivotally carried by hinges 205 and locked to the inner mounting bracket to prevent access to the collected medical waste. The keyed cylinder and locking bar of the lock are in the portion that is broken away from housing 202 in FIG. 7, but the opening 203a engaged by the locking bar is shown in FIG. 7. Materials in the collection station can be thus limited to authorized personnel. The hinge cover 202 may be unlocked by authorized personnel and swung downwardly to the position indicated in FIG. 7A, thereby permitting the removal of the imperforable but breakable container 201 from the inner mounting bracket 203 which supports it within the collection station 200.

Container 201 for used medical waste, such as hypodermic needles, is preferably formed or molded from a material which cannot be perforated by such sharp, solid waste as used needles but which will break or fractionate or shatter when impacted. A preferable such material is clear molded polystyrene of the type commonly used for inexpensive drinking utensils. The container 201 may be molded in a glass or cup-like shape as shown in FIG. 7, with thin walls on the order of about 1/32 to about 1/16 inch thick to provide safety in handling of its contents after collection at the collection station 200. Preferably, a molded polystyrene cover with downwardly turned lip adapted to snap fit over the open top of the container 201 can provide the container 201 with an imperforable but breakable cover (indicated at 201a on FIG. 9) for the further safe handling of the container's contents after its collection. While clear polystyrene is a preferable material for container 201 because of its low cost, transparency, imperforability and its desirable degree of breakability, other materials, such as glass, may be used for container 201.

Where the description above refers to used hypodermic needles, it should be recognized that not only the needle portion but the entire syringe may be collected in container 201 for safe disposal. In addition, disposable scalpels and other sharp solid medical waste and even soft medical waste may be collected at collection station 200 in container 201 for safe handling.

Figure 2:
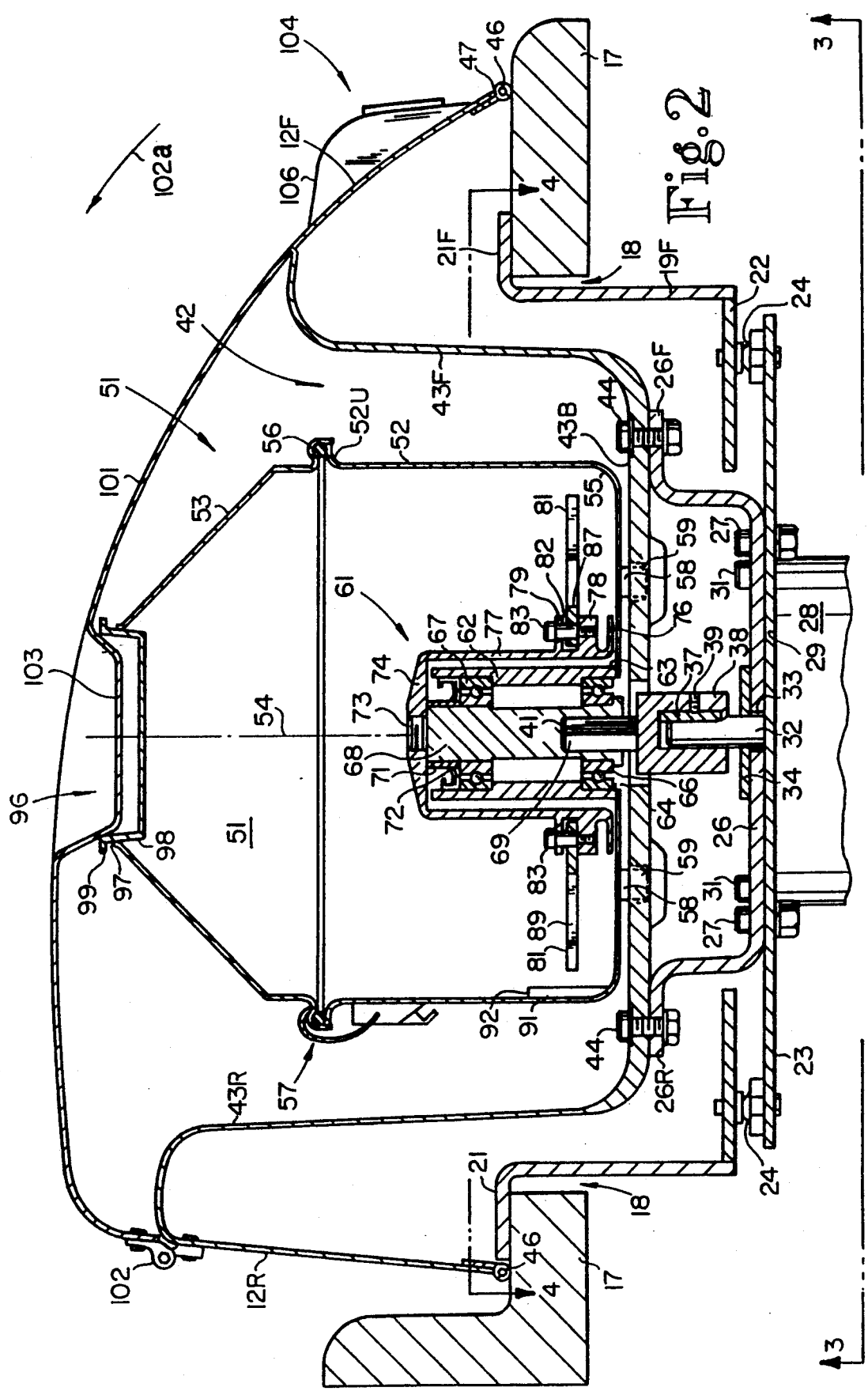
FIG. 2 is an enlarged fragmentary vertical section through a portion of the cabinet taken at line 2—2 in FIG. 1 and viewed in the direction of the arrows and showing some interior details.
Figure 3:
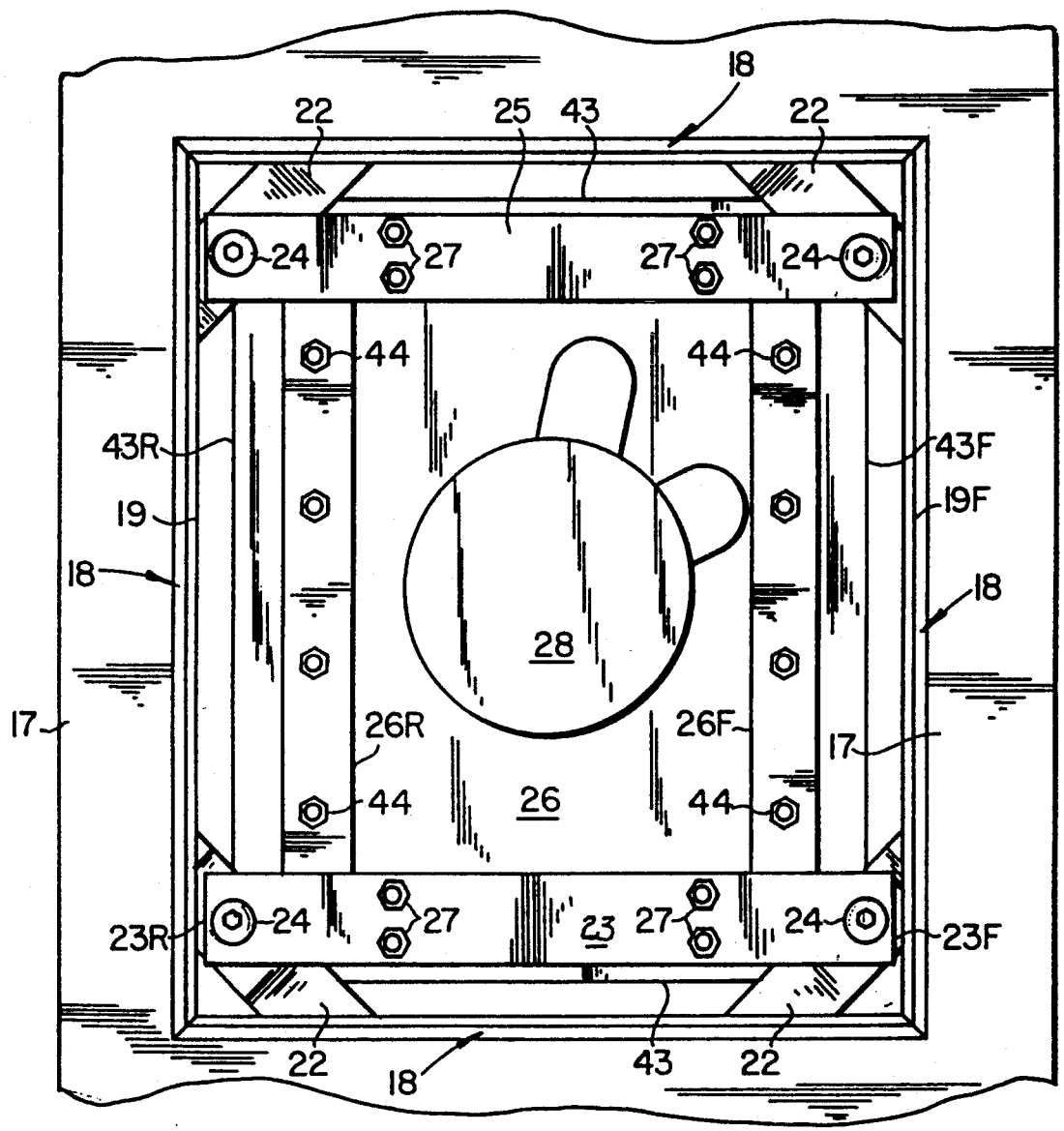
FIG. 3 is a fragmentary section taken at line 3—3 in FIG. 2 and viewed in the direction of the arrows.
Figure 8:
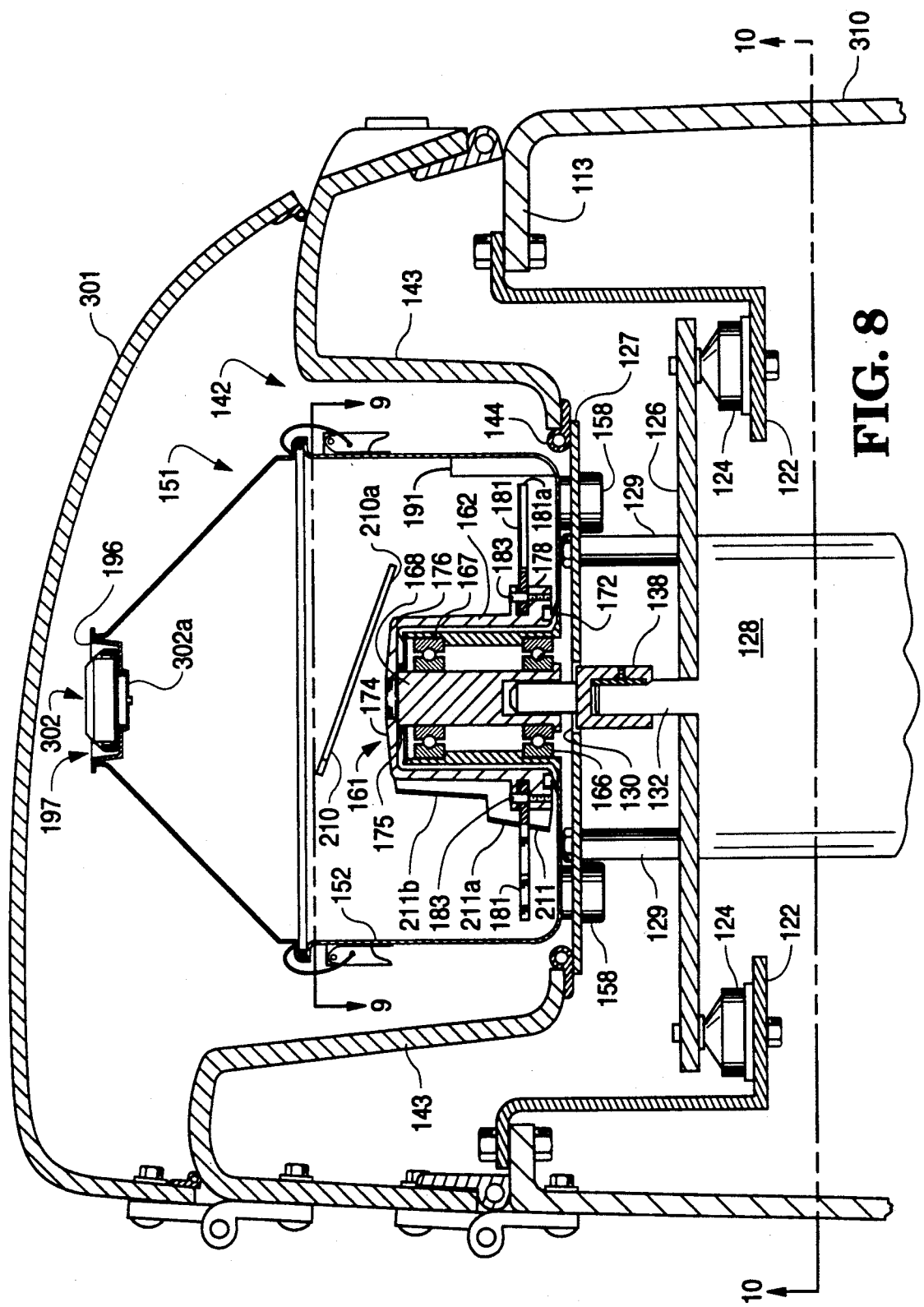
FIG. 8 is a cross-sectional view of a further preferred embodiment of the invention, taken at a central plane through apparatus at line 2—2 in FIG. 1.

Following the collection of solid medical waste in container 201, the entire container may be carried to and inserted in the waste treatment chamber of the type shown in FIGS. 2 and 8 for disposal. The container 201 carrying the solid medical may be inserted through the opening to the chamber (97 in FIG. 2 and 197 in FIG. 8) for destruction. As indicated in phantom lines in FIG. 9, container 201 will be impacted by one of the rotating edges of the rotating assembly within the chamber and will be shattered or fractionated, spilling its contents in the interior of the waste destruction chamber. In the chamber, used hypodermic needles and syringes and the pieces of the container 201 will be driven around the chamber being impacted by the pivotable blades 81, 181, and impacting the abutment surfaces of the abutment bars 91, 191, thereby breaking the larger pieces to small minced solid waste, bunting the tips and sharp edges of the needles, syringes, scalpels and the like and scrubbing the surfaces of the waste with disinfectant.

Figure 9:
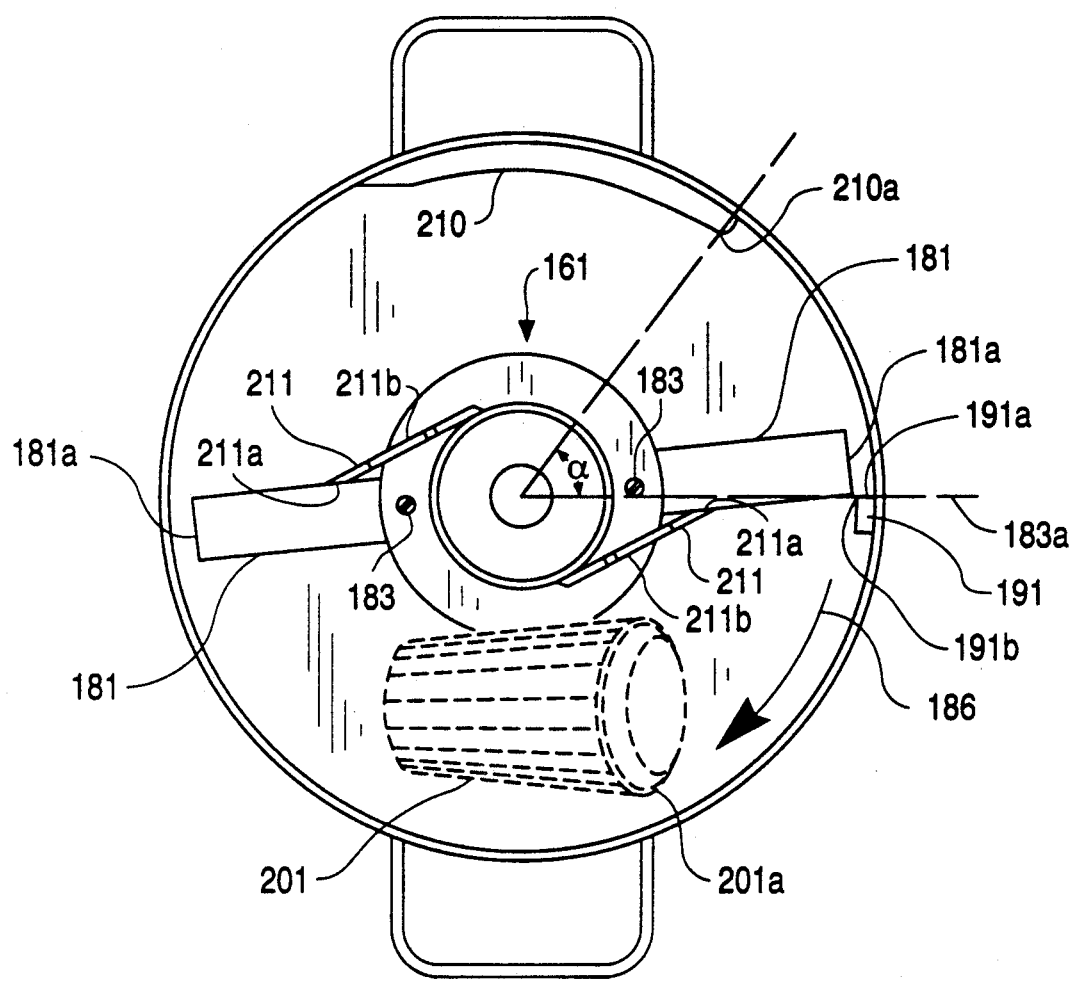
FIG. 9 is a view looking downwardly into the apparatus of FIG. 8 at line 9—9 of FIG. 8, showing in phantom lines a breakable container for the collection of medical waste.

FIG. 8 is a cross-sectional view of a preferred embodiment of the waste treatment apparatus of the invention and FIG. 9 is a view downwardly into the interior of the medical waste treatment chamber of the FIG. 8 apparatus.

The preferred apparatus of FIGS. 8 and 9 is in most respects identical to that shown and described above. Unlike the apparatus shown in FIG. 2, however, the underside of the hinged lid 301 of the apparatus shown in FIG. 8 does not include an inwardly projecting bulge, like bulge 103 in the apparatus of FIG. 2 which engaged the flask closure 96 to ensure that it would remain in place in the chamber opening.

Figure 10:
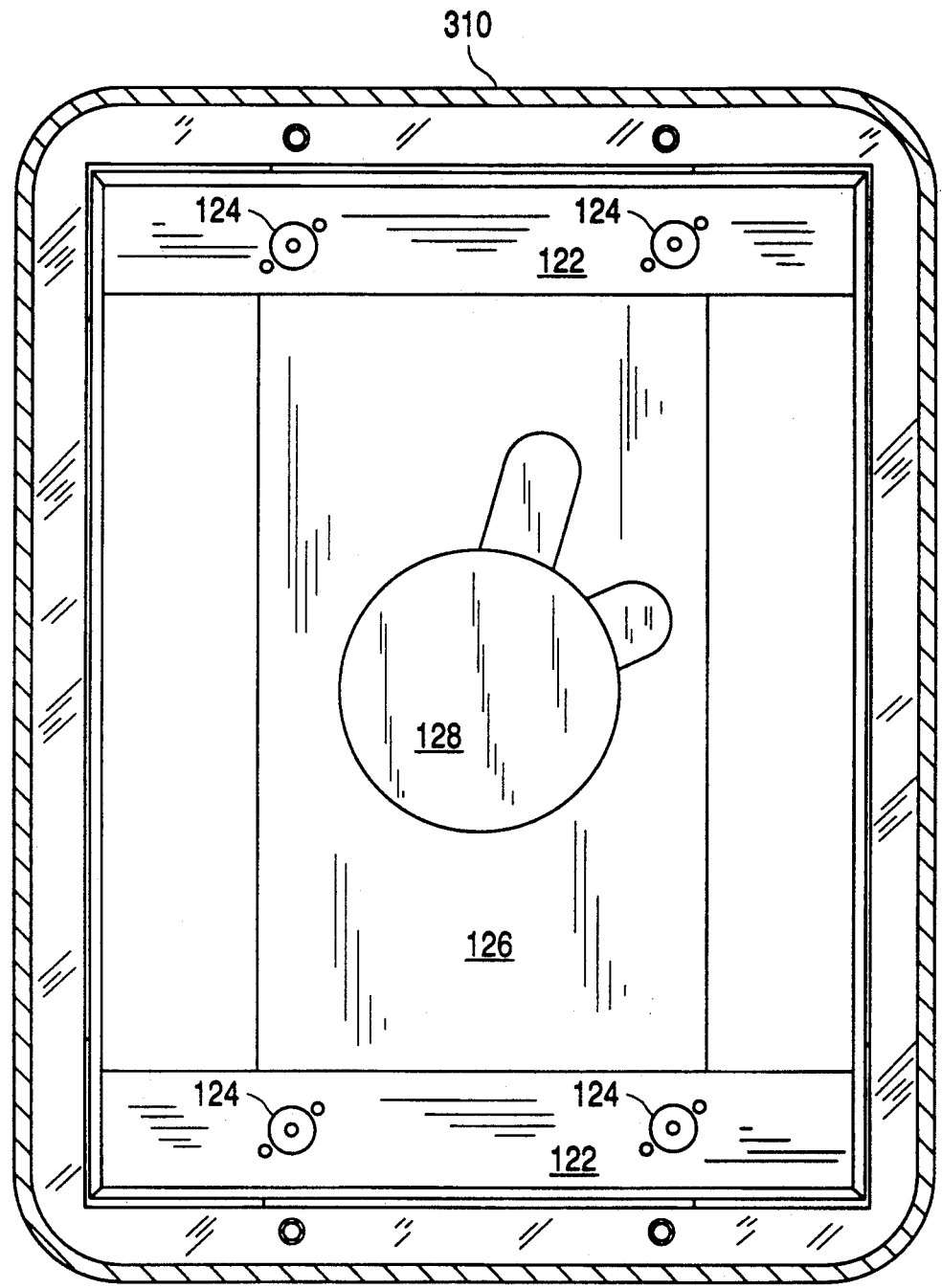
FIG. 10 is a cross-sectional view taken at line 10—10 of FIG. 8 and viewed in the direction of the arrows.
Figure 11:
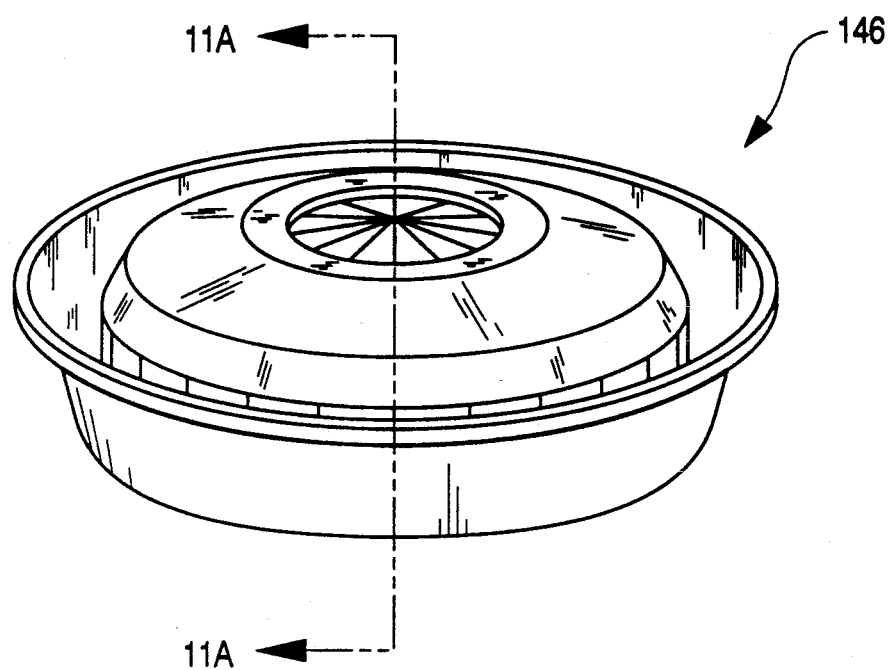
FIG. 11 is a perspective view of the waste treatment chamber closure.
Figure 11A:
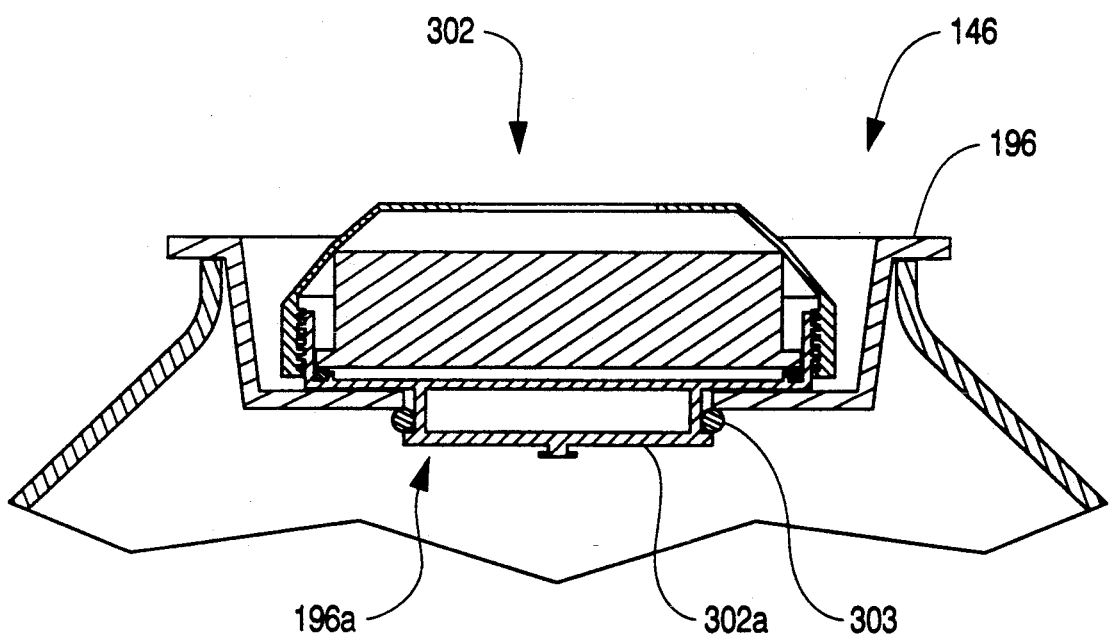
FIG. 11A is a cross-section of the waste treatment chamber closure taken at line 11A—11A of FIG. 11 and in the direction of the arrows.

In the apparatus to FIGS. 7-12, the closable chamber opening 197 is closed by a removable filter cap 196, as shown in greater detail in FIGS. 11 and 11A. Removable filter cap 196 carries a high-efficiency particulate air filter HEDA 302 of the type sold by the 3M Company as their filter Number 7255. The particulate air filter 302 is fitted to an opening 196a in the removable filter cap 196, which is otherwise identical to the cap 96 shown in FIG. 2. The particulate air filter 302 extends downwardly through the opening 196a formed in the base of cap 196 and is held in the cap by an O-ring 303 fitted over the filter portion 302a, which not only holds filter 302 to cap 196 but also seals the interface between the filter 302 and the cap 196. The O-ring retention of particulate air filter 302 thus permits an inexpensive method of fastening and sealing the particulate air filter 302 to the cap 196 and its simple replacement, if necessary. Particulate air filter 302 permits the passage of air and water vapor from the chamber during operation of the waste treatment apparatus but prevents aerosols and fine particles from escaping. Heat generated by the waste treatment within the chamber creates an expansion of the air and water vapor within the chamber which would tend to dislodge cap 196 from opening 197 in the absence of the particulate air filter 302.

As shown in FIGS. 8 and 9, a preferred apparatus of the invention includes a radially extending surface 210 on the chamber sidewall 152. Surface 210 is positioned to direct medical waste materials moving within the chamber to expose it to the coaction of the abutment bar 191 and pivotal blades 181. As shown in FIGS. 8 and 9, the radially extending surface 210 is preferably a ribbon of stainless steel having a thickness on the order of about 3/16 to about ⅜ of an inch and welded (or otherwise fastened) to the sidewall 152 of the chamber in a downwardly extending direction from adjacent the upper portion of sidewall 152 to adjacent the central portion of chamber sidewall 152 so that waste materials will, for example, leave the terminal portion 210a with the velocity directed at abutment bar 191. As indicated above and shown in FIG. 9, abutment bar 191 provides an abutment surface 191a extending radially inward from the container sidewall 152 against which the rotating waste materials impinge. Abutment bar 191 further provides a cutting edge at corner 191b which is located only a small clearance distance from the ends 181a of the blades 181, as indicated in FIGS. 8 and 9. The coaction of blade ends 181a, the abutment surface 191a and cutting edge 191b of abutment bar 191 cut and tear soft medical waste material, such as those described above, into small pieces, and fractionate and dull solid medical waste of the type described above into a generally minced condition. It will be noted that the radially extending surface 210 tends to direct materials adjacent the abutment bar 191 for exposure to this coaction. In preferred embodiments of the invention, the terminal portion 210a of the material deflector 210 is located "upstream" of the abutment surface 191a and cutting edge 191b, and the included angle $\alpha$ between its termination 210a and the surface 191a of the abutment bar lies in the range of 40°-90° to avoid entrapment and lodging of the waste material therebetween.

The preferred apparatus, as shown in FIGS. 8 and 9, further includes a pair of fenders 211 (only one of which is shown in FIG. 8) affixed to the rotatable hub 161 adjacent the pivotable mountings 183 for the waste treating blades 181 and extending downwardly below the blade support flange 178 to a small clearance above the chamber bottom. The fenders 211 thus prevent soft medical waste material, such as cloth and plastic dressings and rubber gloves, from collecting under the blade supporting flange 178 where they may slow the rotation of the rotating hub 161 and rob the rotating waste treatment assembly of power. Fenders 211 sweep such waste material outwardly and impel it against the container sidewalls 152 for impingement by the abutment bar 191 and pivotable blades 181 and destruction thereby.

As shown in FIG. 9, placement of the rigid fenders 211 adjacent the pivotable mountings 183 of the waste treating blades 181 can provide surfaces 211a that impede the rotation of the waste treating blades 181 in the direction of rotation, as shown by arrow 186, forwardly of a radial line 183a extending outwardly from their pivotal mountings 183. If the pivotable blades 181 pivot in the direction of rotation in a direction forwardly of a radial line 183a from the center of the rotating head 161 through their pivotable mountings 183, the blades will tend to draw waste material toward the center of the chamber.

As shown in FIG. 9, the fenders 211 are raked to form a forwardly facing acute angle adjacent the blade supporting hub 178 to reduce drag and assist the action of fenders 211 in sweeping waste material toward the sidewalls 152 of the chamber and the abutment bar 191.

As further shown in FIGS. 8 and 9, fenders 211 may be formed by a pair of metal members that extend upwardly along the rotating hub 161 into the central portion of the chamber to provide an upper rotating edge 211b. The rotating edge 211b can be adapted to fractionalize larger breakable containers 201 which may be inserted within the waste treatment chamber.

As shown in FIG. 8, the rotating hub assembly 161 includes a seal-carrying groove formed in the lower surface of the rotating blade flange 178 and carries a rotating lip seal 172 between the bottom of the rotating blade hub portion 178 and the bottom of the chamber-forming flask assembly 151. The rotating V-ring seal 172 in cooperation with a V-ring seal 175 compressed between the top 174 of the impeller hub and a bearing protection plate 176 protect bearings 166 and 167 from chamber contents.

As with the apparatus shown in FIG. 2, the apparatus of FIGS. 7-12 includes a lower ball bearing assembly 166 and an upper ball bearing assembly 167 spaced several inches apart, and supported by, a bearing supporting cylinder 162, which is welded to the bottom of the flask assembly 151. The inner race of bearings 166 and 167 carry the impeller shaft 168. This assembly provides a rugged and durable rotatable support of the rotating waste destruction and treatment assembly (which includes pivotal blades 81, 81 and rotating fenders and edges 211, 211b), which must endure intense shock loads in operation. The combination of the pivotable blades, which are pivotally mounted intermediate the upper and lower bearings 166 and 167, and the spaced ball bearing support provided the impeller shaft provide a waste treatment assembly which can endure the torturous abuse imposed by the combined effects of solid and/or soft medical waste being processed.

Figure 12:
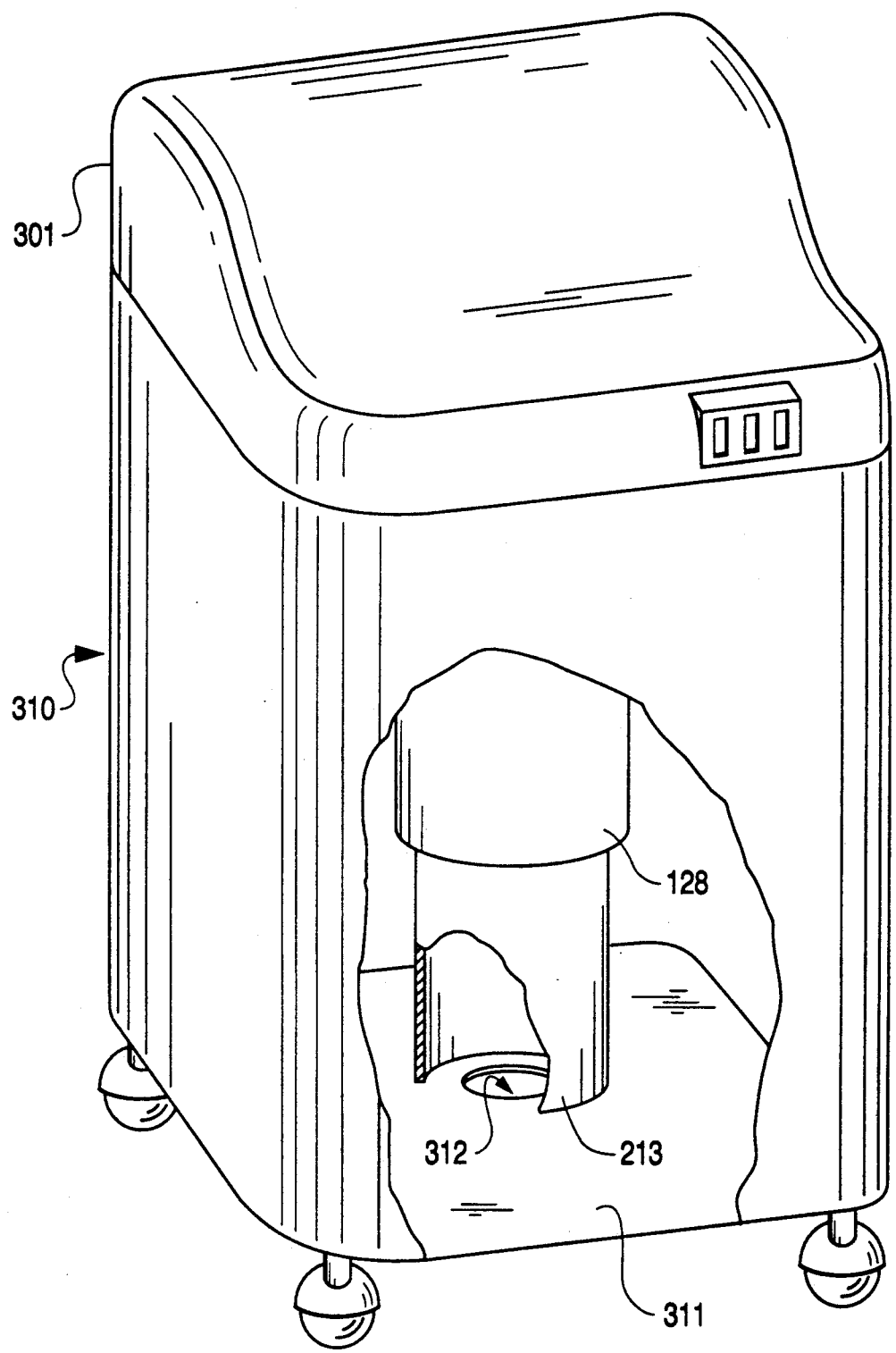
FIG. 12 is a partially broken away perspective view of a waste treatment system of the invention.

As shown in FIG. 12, in the apparatus, the cart enclosing the apparatus forms a walled enclosure 310 for the operational portions of the waste treatment apparatus including the chamber forming means shown in FIGS. 2, 8 and 9 and the driving motor 28, 128 for the rotating hub assembly 61, 161. The walled enclosure 310 includes a bottom 311 with an opening 312 for motor cooling air. As shown and described above, the walled enclosure provided by the cart also includes an openable top 301 which can be opened to permit access to the waste treatment chamber.

In the preferred embodiment of the invention shown in FIG. 12, an elastomeric cylinder 213 is located between the enclosure bottom 311 and the motor 128. The elastomeric cylinder 213 surrounds the cooling air opening 312 in the enclosure bottom 311. The elastomeric cylinder 213 has sufficient axial length that it is slightly compressed between the motor 128 and the enclosure bottom 311 and forms a duct for cooling air between the cooling opening 312 and the cooling air inlets in the end flange of motor 128. The elastomeric cylinder 213 also acts as a sound muffler, impeding the escape of sound from the walled enclosure 310 through the cooling air opening 312.

Referring now to FIGS. 8 and 10, the motor 128 is securely mounted at its upper end to a support plate 126 which is carried by a plurality of vibration isolator couplings 124 to a pair of isolation bars 122 which are carried from the top 113 of the walled enclosure 310. A receiving plate 127 for the chamber-forming flask assembly 151 is carried above support plate 126 by a plurality of tubular spacers 129 The receiving plate 127 includes four spaced holes adapted to receive the four feet 158 of the flask assembly 151 in a manner like that described for the apparatus of FIG. 2. Receiving plate 127 has a central opening 130 which permits a driving coupling 138 from the rotating shaft 132 of the driving motor to extend into the keyed opening of the impeller shaft 168 of the rotating hub assembly 161. Thus, the entire rotational waste treatment assembly and its driving motor are suspended within the walled enclosure and openable top by a vibration isolating structure. There is no mechanical connection between the sidewalls 143 of the centralized tub portion 142 of the enclosure and the flask receiving plate 127 or any other portion of the waste treatment operating apparatus. An elastomeric gasket 144 is mounted to the opening in the centralized tub portion 142 of the apparatus enclosure. The elastomeric flange may be fastened to the sidewalls 143 of the centralized tub portion 142 by any convenient manner for example by an appropriate adhesive. The elastomeric gasket 144 and cylinder 213 tend to absorb and dampen vibration of the operating waste treatment assembly.

Thus, in the preferred apparatus of the invention shown in FIGS. 7-12, vibration and sound are trapped and deadened in an improved manner within the enclosure for the apparatus, and the operating portion of the waste treatment apparatus including the flask assembly, driving motor and the intervening supporting structure, are isolated from the enclosure by elastomeric sound and vibration deadening elements. The driving motor and waste destruction chamber are thus isolated from the apparatus housing.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of treatment of medical waste material comprising the steps of:
   depositing medical waste material in a breakable container at a site of generation by providing an imperforable but breakable container in a separate lockable collection housing having an opening communicating with the container interior;
   locking said collection housing;
   inserting medical waste material through the opening of the lockable collection housing into the imperforable but breakable container; and
   depositing the breakable container with its contained medical waste material in a waste treatment apparatus and operating the waste treatment apparatus to fractionate and disinfect the breakable container and its contained medical waste material.

2. The method of claim 1 further comprising covering the container with an imperforable but breakable cover before removing the container from said collection housing.

3. A method of treating solid and soft medical waste, comprising:
  providing a portable, closeable medical waste processing assembly;
  lacing medical waste material into said portable, closeable medical waste processing assembly;
  placing a chemical disinfecting agent into the portable closeable medical waste processing assembly;
  closing the portable, closeable medical waste processing assembly for processing;
  imposing high velocity on the medical waste material with both radial and tangential velocity components while within the portable, closeable medical waste processing assembly;
  providing abutment and cutting surfaces within the portable, closeable medical waste processing assembly;
  directing the medical waste to the abutment and cutting surfaces within the portable, closeable medical waste processing assembly;
  cutting and tearing soft medical waste and fractionating and blunting solid medical waste to small, minced solid waste within the portable, closeable medical waste processing assembly; and
  washing the cut and torn soft medical waste and fractionated and blunted solid medical waste with the chemical disinfecting agent during processing within the portable, closeable medical waste processing assembly.

4. The method of claim 3 including the step of placing the medical waste in a closeable breakable container as it is generated, closing the closeable breakable container to further contain medical waste within the closeable breakable container, placing the closed breakable container and its medical waste contents into the portable closeable medical waste processing assembly, carrying the closeable portable medical waste processing assembly to a separate power unit, placing the closeable portable medical waste processing assembly on the separate power unit, operating the separate power unit and fractionating the closed breakable container and its closure to comminute and disinfect the closed breakable container, its closure and the container contents.

5. The method of claim 3 including imparting high velocity to the medical waste material within the portable closeable medical waste processing assembly by a plurality of rotating pivotable blades that are rotated in excess of 3500 rpm.

6. The method of claim 5 including cutting and tearing non-solid medical waste and fractionating and blunting solid medical waste with abutment and cutting surfaces provided in an internal sidewall of the portable closeable medical waste processing assembly and by the rotating pivotable blades.

7. The method of claim 3 including imparting high velocity on the medical waste by a plurality of rotating fenders on a rotating waste treatment assembly.

8. A medical waste treatment system, comprising:
  a medical waste collection station comprising an imperforable but breakable waste container with a closeable opening, a lockable housing supporting and containing said waste container and providing restricted access to said container, said lockable housing having an opening permitting medical waste to be deposited within the container; and
  a portable medical waste treatment apparatus comprising a closeable waste treatment chamber with an opening permitting the insertion of the imperforable but breakable container, and a rotatable waste treatment assembly within said closeable waste treatment chamber connected to a separate driving motor so that upon connection to and rotation by said separate driving motor and the insertion of a chemical disinfectant into the closeable waste treatment chamber, the rotatable waste treatment assembly breaks and fractionates said container and its contents and disinfects the container and its contents.

9. In a medical waste treatment apparatus comprising a closeable chamber, including a bottom, a sidewall and a top, for the collection and treatment of solid and soft medical waste, and a plurality of waste treating blades pivotally mounted on a rotatable hub to rotate within said closeable chamber adjacent its bottom, the improvement comprising a plurality of rigid fenders fixed to the rotatable hub, each of said plurality of rigid fenders being carried adjacent the pivotal mounting of one of said plurality of waste treating blades and extending downwardly from said rotatable hub to a small clearance space above the chamber bottom.

10. The apparatus of claim 9 wherein each of said rigid fenders provide a surface impeding the pivoting of said pivotal blades in the direction of rotation of said rotatable hub.

11. The apparatus of claim 9 wherein said fenders are raked to form a forwardly facing surface lying at an acute angle with respect to a radial line extending from the rotatable hub through the fenders.

12. The apparatus of claim 9 wherein said rotatable hub includes a rotating sidewall extending upwardly into said chamber and wherein said rotating sidewall provides an edge rotating therewith to fractionalize a breakable container within said chamber.

13. The apparatus of claim 12 further comprising a breakable container to receive and contain medical waste when outside of said chamber and fractionalize within said chamber to expose said medical waste to treatment.

14. The apparatus of claim 12 wherein said fenders extend upwardly along said rotating sidewall of said rotatable hub and form said rotating edge.

15. Apparatus for the treatment of used hypodermic needles, comprising:
  a breakable container formed of imperforable material with a closeable opening permitting said container to receive and contain used hypodermic needles;
  a portable housing forming a chamber defined by a bottom, sidewall and top and a closeable chamber opening in the top permitting insertion of said breakable container into said chamber;
  a rotatable hub carried by the chamber bottom and a plurality of blades pivotally carried by said rotatable hub; and
  an abutment bar formed on the chamber sidewall and providing an abutment surface projecting from the sidewall and terminating in a cutting edge; and
  a separate power unit including a motor to drive the rotatable hub of said portable housing,
  said rotatable hub, pivotable blades and said abutment bar cooperating, upon insertion of said breakable container and its contents into said chamber through said closeable chamber opening, and upon placement of said portable housing on said separate power unit and rotation of said rotatable hub, to fractionalize and blunt said container and its contents including any used hypodermic needles.

16. The apparatus of claim 15 wherein said rotatable hub carries a fender adjacent each of the plurality of pivotable blades and said fenders extend downwardly from said rotatable hub to a small clearance over said bottom.

17. The apparatus of claim 16 wherein at least one of said fenders includes an upwardly extending portion that forms a rotating edge adapted to fractionalize said breakable container.

18. The apparatus of claim 16 wherein each of said fenders forms a surface lying at a forwardly facing acute angle with respect to a radial line extending through the fender and a surface impeding the pivoting of the adjacent blade forwardly of a radially extending line through its pivot in the direction of rotation.

19. In a medical waste treatment apparatus comprising a closeable chamber including a bottom, a sidewall and a top that forms a closeable chamber opening, and a rotating waste treatment assembly within said chamber for destruction and disinfection of medical waste, and a closure for said chamber opening, the improvement wherein said closure comprises:
- a removable filter cap carrying a higher efficiency particular air filter permitting the passage of air and water vapor from the chamber and trapping aerosols and fine particles, said air filter including a portion extending downwardly through an opening in said removable filter cap, and
- an O-ring fitting over the portion of said air filter extending through the opening of said removable filter cap to retain said air filter in said filter cap and seal the interface therebetween.

20. In a medical waste treatment apparatus comprising a portable closeable chamber including a bottom, a sidewall and a top forming a closeable opening, a rotating waste treatment system comprising a plurality of pivotable blades, and an abutment bar and sidewall providing an abutment surface and cutting edge, said blades and abutment bar cooperating to destroy medical waste placed in the chamber, the improvement comprising:
- a radially extending surface on the chamber sidewall positioned to direct medical waste moving within said chamber in response to rotation of said rotating waste treatment system to adjacent the abutment bar.

21. The apparatus of claim 20 wherein said radially extending surface extends around the sidewall of the chamber in a downwardly extending direction.

22. In a medical waste treatment apparatus comprising means forming a chamber to receive and treat solid and soft medical waste, a rotating waste treatment assembly within said chamber, a motor to drive the rotating waste treatment assembly, and a walled enclosure for said chamber forming means and said driving motor including a plurality of sidewalls and an openable top to permit access to said chamber forming means, wherein said chamber forming means is separable from said medical waste treatment apparatus, with a plurality of feet on its bottom, and wherein said walled enclosure supports said separable chamber forming means and driving motor, the further improvement wherein a support plate carries a chamber receiving plate supporting said separable chamber and having a plurality of openings adapted to receive the feet of said separable chamber and further carries said driving motor for the rotating waste treatment assembly, said chamber-receiving plate and support plate having openings permitting mechanical interconnection of the driving motor and rotating waste treatment assembly, said support plate being carried on vibration isolating supports by a plurality of isolation bars, said plurality of isolation bars being carried by said walled enclosure.

23. The apparatus of claim 22 wherein said support plate is carried by four vibration absorbing mounts and two elongated isolation bars from said walled enclosure sidewall, with one bar and two vibration-absorbing mounts being located at opposing sides of the support plate.

24. Apparatus for the treatment of used hypodermic needles, comprising:
- a breakable container formed of imperforable material with an opening permitting said container to receive and contain used hypodermic needles;
- a housing forming a chamber defined by a bottom, sidewall and top and a closeable chamber opening in the top permitting insertion of said breakable container into said chamber;
- a rotatable hub carried by the chamber bottom, a plurality of blades pivotally carried by said rotating hub and a fender carried by said rotatable hub adjacent each of the plurality of pivotable blades, said fenders extending downwardly from said rotatable hub to a small clearance over said bottom; and
- an abutment bar formed on the chamber sidewall and providing an abutment surface projecting from the sidewall and terminating in a cutting edge,
- said rotatable hub, pivotable blades and abutment bar cooperating, upon insertion of said breakable container and its used hypodermic needle contents into said chamber through said closeable chamber opening and upon rotation of said rotatable hub, to fractionalize and blunt said container and used hypodermic needles.

25. The apparatus of claim 24 wherein at least one of said fenders includes an upwardly extending portion that forms a rotating edge to fractionalize said breakable container.

26. The apparatus of claim 24 wherein each of said fenders forms a surface lying at a forwardly facing acute angle with respect to a radial line extending through the fender and a surface impeding the pivoting of the adjacent blade forwardly of a radially extending line through its pivot in the direction of rotation.

27. An apparatus for the disintegration and disinfection of medical waste, comprising:
- a separate portable closeable medical waste processing assembly comprising a medical waste processing chamber formed by a bottom, sidewall and a top including a closeable opening;
- a bearing support projecting upwardly from the bottom of the separate portable closeable medical waste processing assembly and carrying a lower ball bearing adjacent the bottom of the chamber and an upper ball bearing spaced above the lower ball bearing, said upper and lower ball bearings having their outer races carried by said bearing support and their inner races carrying an impeller shaft for a rotating waste destruction and treatment assembly within the medical waste processing chamber;

said rotating waste destruction and treatment assembly comprising a pair of pivoting blades being pivotably carried by said rotating waste destruction and treatment assembly outwardly of and adjacent to said lower ball bearing and adjacent the bottom of said medical waste processing chamber;

said sidewall of said medical waste processing chamber having an abutment surface extending inwardly therefrom and terminating in a cutting edge located in close proximity to the outer ends of the pivoting blades when said blades are fully extended; and a separate power unit comprising a drive motor, for rapid rotation of said rotating waste destruction and treatment assembly, carried by said separate power unit with its drive shaft extending upwardly through a horizontal power unit surface that supports the separate portable medical waste processing assembly and with the impeller shaft for the rotating waste destruction and treatment assembly in engagement with the drive shaft of the drive motor.

28. The apparatus of claim 27 wherein the rotating waste destruction and treatment assembly includes a pair of rigid surfaces adjacent the pivotable mounting of said pivoting blades to prevent the pivoting of pivoting blades in the direction of rotation of the rotating waste destruction and treatment assembly.

29. The apparatus of claim 28 wherein said pivoting blades include lower surfaces that are inclined downwardly from their leading edges and wherein said rotating waste destruction and treatment assembly further includes a pair of fenders extending downwardly from adjacent said pair of pivoting blades from forwardly thereof in the direction of rotation and terminating just above the bottom of the medical waste processing chamber.

30. The apparatus of claim 27 further comprising a surface extending radially inwardly from said sidewall of said medical waste processing chamber from above said pivoting blades and extending downwardly toward said abutment surface.

31. The apparatus of claim 27 wherein said closeable opening of the medical waste treatment chamber is closed by a removable filter cap that carries a removable HEPA filter in an opening closed by said HEPA filter.

32. The apparatus of claim 31 wherein said opening of said removable filter cap has a circular periphery, and said removable HEPA filter has a circular portion that extends through the opening of said filter cap and carries an O-ring that both seals the interface between said removable filter cap and removable HEPA filter and retains said removable HEPA filter in said opening.

33. The apparatus of claim 27 wherein said rotating waste destruction and treatment assembly includes a pair of fenders forming a pair of rotating surfaces extending upwardly from adjacent to said pair of pivoting blades.

34. The apparatus of claim 33 wherein said pair of fenders also extends downwardly from adjacent said pair of pivoting blades to provide a small clearance space above the bottom of the medical waste treatment chamber.

35. The apparatus of claim 34 wherein said pair of fenders provides surfaces impeding the pivoting of the pivoting blades forwardly in the direction of their rotation.

36. The apparatus of claim 35 wherein each of said pair of fenders forms a surface lying at a forwardly facing acute angle with respect to a radial line extending through the fender.

* * * * *

UNITED STATES PATENT AND TRADEMARK OFFICE
CERTIFICATE OF CORRECTION

PATENT NO. : 5,236,135

DATED : August 17, 1993

INVENTOR(S) : Joseph H. Wilson, et al.

It is certified that error appears in the above-identified patent and that said Letters Patent is hereby corrected as shown below:

In Col. 1, line 41, after "trash", insert --.-- (a period).

In Col. 1, line 42, after "items", insert --.-- (a period).

In Col. 2, line 38, after "poured", insert --.-- (a period).

In Col. 6, line 55, before "opening", delete "to".

In Col. 6, line 58, after "example", insert --.-- (a period).

In Col. 7, line 33, delete "nd" and insert therefor --end--.

In Col. 9, line 26, after "medical", insert --waste--.

In Col. 9, line 54, delete "to" and insert therefor --of--.

In Col. 9, line 58, delete "HEDA".

In Col. 11, line 38, after "81," delete "8" (second occurrence) and insert therefor --,181--.

UNITED STATES PATENT AND TRADEMARK OFFICE
CERTIFICATE OF CORRECTION

PATENT NO. : 5,236,135

DATED : August 17, 1993

INVENTOR(S) : Joseph H. Wilson, et al.

It is certified that error appears in the above-identified patent and that said Letters Patent is hereby corrected as shown below:

In Col. 12, line 10, after "129", insert --.-- (a period).

In Col. 14, line 63, between "from" and "the" insert a space.

Signed and Sealed this

Thirtieth Day of August, 1994

Attest:

BRUCE LEHMAN

Attesting Officer

Commissioner of Patents and Trademarks